United States Patent
Bastioli et al.

(10) Patent No.: US 10,294,442 B2
(45) Date of Patent: May 21, 2019

(54) PROCESS FOR THE FRACTIONATION OF SEEDS FROM OLEAGINOUS PLANTS

(71) Applicant: Novamont S.p.A., Novara (IT)

(72) Inventors: Catia Bastioli, Novara (IT); Giampietro Borsotti, Novara (IT); Luigi Capuzzi, Novara (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 15/548,218

(22) PCT Filed: Feb. 5, 2016

(86) PCT No.: PCT/EP2016/052539
§ 371 (c)(1),
(2) Date: Aug. 2, 2017

(87) PCT Pub. No.: WO2016/124754
PCT Pub. Date: Aug. 11, 2016

(65) Prior Publication Data
US 2018/0023030 A1    Jan. 25, 2018

(30) Foreign Application Priority Data
Feb. 5, 2015 (IT) .................. 102015000005543

(51) Int. Cl.
| | | |
|---|---|---|
| C11B 1/04 | (2006.01) | |
| C11B 1/06 | (2006.01) | |
| C11B 1/10 | (2006.01) | |
| A61K 36/28 | (2006.01) | |
| A61K 8/92 | (2006.01) | |
| A61K 8/97 | (2017.01) | |
| A61K 31/7048 | (2006.01) | |
| A61K 45/06 | (2006.01) | |
| C11B 1/08 | (2006.01) | |
| A23K 10/37 | (2016.01) | |
| A61Q 19/00 | (2006.01) | |
| C11B 13/00 | (2006.01) | |

(52) U.S. Cl.
CPC .............. *C11B 1/04* (2013.01); *A23K 10/37* (2016.05); *A61K 8/922* (2013.01); *A61K 8/97* (2013.01); *A61K 31/7048* (2013.01); *A61K 36/28* (2013.01); *A61K 45/06* (2013.01); *C11B 1/06* (2013.01); *C11B 1/08* (2013.01); *C11B 1/10* (2013.01); *A61K 2800/10* (2013.01); *A61K 2800/80* (2013.01); *A61K 2800/805* (2013.01); *A61Q 19/00* (2013.01); *C11B 13/00* (2013.01); *Y02P 60/877* (2015.11); *Y02W 30/74* (2015.05)

(58) Field of Classification Search
CPC ..... C11B 1/04; C11B 1/06; C11B 1/08; C11B 1/10; A61K 36/28
See application file for complete search history.

(56) References Cited

U.S. PATENT DOCUMENTS

| | | | | |
|---|---|---|---|---|
| 2003/0072866 A1* | 4/2003 | Higgs | ................ | A23J 1/14 426/618 |
| 2006/0246153 A1* | 11/2006 | Bombardelli | .......... | A61K 31/01 424/641 |
| 2007/0110704 A1* | 5/2007 | Gallinat | .................. | A61K 8/35 424/74 |
| 2010/0104524 A1* | 4/2010 | Lee | ...................... | A61K 8/4973 424/62 |
| 2014/0037770 A1* | 2/2014 | Okubo | ................ | A61K 31/365 424/764 |

FOREIGN PATENT DOCUMENTS

| | | | | |
|---|---|---|---|---|
| EP | 2020238 A1 | 2/2009 | | |
| EP | 2623107 A1 | 8/2013 | | |
| WO | WO-2008/024840 A2 | 2/2008 | | |
| WO | WO-2008024840 A2 * | 2/2008 | ............... | A23J 1/14 |
| WO | WO-2013/139839 A2 | 9/2013 | | |

OTHER PUBLICATIONS

Lilla Szokol-Borsodi et al., Optimum yields of dibenzylbutyrolactone-type lignans from cynareae fruits, during their ripening, germinatin and enzymatic hydrolysis process, determined by on-line chromatographic methods, 2012, Phytochemical Analysis, vol. 23, No. 6, pp. 598-603 Year 2012.*

Boldizsar et al., Complementary fragmentation pattern analysis by gas chromatography-mass spectrometry and liquid chromatography tandem mass spectrometry confirmed the precious lignan content of Cirsium weeds, 2010, Journal of Chromatography A, vol. 1217, No. 40pp. 6281-6289 Year 2010.*

Inagaki, I., et al., Lignans of Trachelospermum asiaticum var. intermedium. I(1) Isolation and structures of Arctiin, Matairesinoside and Tracheloside, 1972, Chem. Pharm. Bull., vol. 20, issue 2, pp. 2710-2718 (Year: 1972).*

Susanne Kuehnl et al., "Lignans from Carthamus tinctorius suppress tryptophan breakdown viai ndolearnine 2,3-dioxygenase", Phytomedicine 20 (2013)1190-1195.

S. Celik et al., "Guaianolides and lignans from the aerial parts of Centaurea ptosimopappa", Biomchemical Systematics and Ecology 34(4) 2006) 349-352.

* cited by examiner

*Primary Examiner* — Yate' K Cutliff
(74) *Attorney, Agent, or Firm* — Polsinelli PC

(57) ABSTRACT

The invention relates to a process for the fractionation of seeds of oleaginous plants of to the Asteraceae family, comprising at least one mechanical pressing operation of the seeds and an extraction with polar organic solvent of the first residue obtained. Said process allows to separate oil, active substances and a solid residue which is particularly suitable to be used in animal feed. The present invention also relates to said solid residue and to its use for the production of animal feed, as well as to the extracted active substances and to their use as cosmetic and/or pharmaceutical ingredient.

22 Claims, No Drawings

PROCESS FOR THE FRACTIONATION OF SEEDS FROM OLEAGINOUS PLANTS

CROSS REFERENCE TO RELATED APPLICATIONS

This application is a National Phase filing under 35 U.S.C. § 371 of PCT/EP2016/052539 filed on Feb. 5, 2016; and this application claims priority to Application No. 102015000005543 filed in Italy on Feb. 5, 2015 under 35 U.S.C. § 119. The entire contents of each application are hereby incorporated by reference.

This invention relates to a new process for the production of oil, solid residue and active substances from the seeds of oleaginous plants of the Asteraceae family, in particular from *Cynara cardunculus, Sylibum marianum* (milk thistle) and *Carthamus tinctorius* (safflower). In particular this invention relates to a new process whereby starting from the seeds of these plants it is possible to extract oil and obtain a solid residue having a protein content of between 20 and 40% by weight and an extract containing active substances such as polyphenols, in particular some lignans, including Arctiin and/or the corresponding aglycone Arctigenin.

This invention also relates to the said solid residue and its use in feedstuffs for livestock; reference is also made to the said extract containing active substances, and its use in cosmetic and pharmaceutical formulations.

The use of oleaginous plants such as for example soya, peanuts and sunflowers for the production of seeds intended for the extraction of vegetable oils mainly intended for food use is known.

It is also known that a substantial quantity of solid residues having a high protein content which mainly find application in the feedstuffs industry as protein supplements for animal feeds are obtained from the seeds of the said oleaginous plants as a by-product of the oil extraction process.

The possibilities of using the said solid residues are however greatly influenced by the composition of the residues, mainly the quantity and quality of the amino acids, the fibre content and the residual oil content. In fact solid residues having a high level of balanced proteins can be used to optimise the composition of feedstuffs, for example on the basis of the type of livestock for which it is intended. This essentially contributes to maximisation of the nutritive value of the said feeds while at the same time simplifying their production and ultimately containing costs.

In light of the ever-increasing requirement for new feeds having improved nutritional value there is therefore a need to identify new oleaginous species which are capable of providing solid residues with a good balance between the different nutritional components present in them.

The lignan Arctiin and its aglycone Arctigenin have important pharmacological properties. Plant extracts which contain them have been used for some time, for example in traditional Chinese medicine, on account of their anti-inflammatory, immunomodulating, anti-viral and anti-tumoural activities. In addition to anti-inflammatory properties, Arctiin and Arctigenin have also demonstrated that they can stimulate the neosynthesis of collagens and therefore find advantageous application in the cosmetics sector (Journal of Cosmetic Dermatology, 7, 4, 281-289). These substances are generally extracted from herbaceous plants such as the greater burdock (*Arctium lappa*) or Saussurea.

On the basis of the literature, the extraction of oil, active substances and the acquisition of an extraction residue which can be used as animal feed appears to be difficult to incorporate into a single production process.

Starting from this need it has now surprisingly been discovered that it is possible to obtain oil, solid residues capable of expressing the abovementioned properties and active substances from the seeds of oleaginous plants of the Asteraceae family, in particular from *Cynara cardunculus*, milk thistle and safflower, by means of a single process.

The process according to this invention, which comprises at least one stage of mechanical pressing, optionally preceded by grinding of the said seeds, and at least one stage of extraction of the first residue obtained using a polar organic solvent, in fact makes it possible to extract oil, obtain a residue characterised by a protein content and organoleptic characteristics which render it particularly suitable for animal feedstuffs and at the same time to isolate significant quantities of polyphenols, in particular lignans, including the active substance Arctiin, with high added value. Other lignans, such as for example Tracheloside, and other compounds such as flavonolignans can also be isolated.

The object of this invention is in particular a process for the fractionation of seeds from oleaginous plants of the Asteraceae family into oil, solid residue and active substances comprising the stages of:

(a) subjecting the said seeds to at least one mechanical pressing operation, obtaining a first residue and removing at least part of the oil;

(b) subjecting the said first residue to extraction with a polar organic solvent and separating out the remaining solid residue from the resultant liquid phase comprising oil and extracted active substances;

(c) separating the active substances and oil from the said liquid phase in stage b).

The separation in stage (c) is preferably performed through using an apolar solvent, and subsequently separating out an apolar fraction comprising oil from a polar fraction comprising the active substances. As an alternative it may be performed using other techniques known to those skilled in the art, for example by crystallising out the active substances, separating them from the liquid phase from stage (b), by for example filtration, and subsequent removal of the solvent from the extracted oil.

The oleaginous plants comprising the raw material for the process belong to the Asteraceae family, in particular the Cardueae tribe, preferably the species *Cynara cardunculus, Silybum marianum* or *Carthamus tinctorius*.

The plant species belonging to the Cardueae tribe are also very robust annual or perennial herbaceous plants which have the further advantage that they can be cultivated in arid areas with not very favourable climates.

Seeds of *Cynara cardunculus* are particularly suitable for the process. Mixtures of seeds from plants of different species belonging to the Asteraceae family can also be used as raw material, the mixtures comprising seeds of *Cynara cardunculus* being particularly preferred. Through the process according to the invention it is possible to obtain a solid residue having a protein content higher than 20% by weight, advantageously of between 20 and 40% by weight, which can be used for the preparation of livestock feeds, from thistle seeds. The said protein content can be advantageously increased to up than 60% by subjecting it to one or more optional mechanical or electrochemical separation operations, in order to separate a fraction richer in proteins from a fraction richer in cellulose, hemicellulose and lignin.

As far as the protein content of the solid residue is concerned, this may be determined by any of the methods known to those skilled in the art, for example by determining the nitrogen content by means of the Kjeldhal method and multiplying the value obtained by the coefficient 6.25 (which expresses the average nitrogen content of proteins).

The process according to this invention is also particularly flexible in that it makes it possible to modulate the active substances content, in particular that of polyphenols, in the said solid residue. In particular it makes it possible to separate out significant quantities of active substances, typically between 0.5 and 12% with respect to the weight of the starting seed, which can be determined using any of the methods known to those skilled in the art, for example by chromatography.

At the time of harvesting and transport the seeds are generally contaminated by foreign bodies of various kinds such as for example stones, earth and even ferrous residues originating for example from the equipment used in harvesting. These seeds may also contain a high moisture content and have husks or be of a size which might influence the pressing and extraction stages in the process, depending upon the methods of operation used. The process according to this invention can therefore optionally comprise one or more preliminary stages of treatment of the seeds prior to stage (a), selected from:

(i) cleaning and screening,
(ii) decorticating,
(iii) drying,
(iv) comminuting and/or grinding.

These preliminary stages of treatment of the seeds may be combined together at different times. According to a preferred aspect of this invention the process comprises preliminary stages (i) and (iii), preferably in the order indicated, i.e. first the stage of cleaning the seeds and subsequently the stage of drying the cleaned and screened seeds.

The preliminary stage of cleaning and screening (or sieving) the seeds (i) is typically performed by passing the seeds through vibrating screens or sieves, aspiration systems or electromagnetic systems.

Resorting to decorticating or dehusking stage (ii), eliminating a component of the seeds having a low protein content and rich in lignin, makes it possible to increase the protein content of the solid residue and its digestibility. When it is performed this dehusking generally takes place after stage (i) and before stage (iii), typically by causing the seeds to pass through equipment capable of removing the husk (pericarp, head) from the seeds, such as for example cylinder or disc dehuskers. The principle on which both of these types of dehusker work is the same—they apply slight pressure to the seed causing the pericarp to open and subsequently separate the body of the seed (the kernel) from the same, which is then removed for example by means of a screening system or a jet of air.

The optional stage of drying or dewatering (iii) makes it possible to control the water content of the seeds. The purpose of this is mainly to limit phenomena which deteriorate the seeds, thus making longer storage possible and also contributing to a satisfactory outcome for subsequent stage (a). For example too low a water content may give rise to excessive fragmentation of the seeds, with the consequent formation of dusts.

The drying stage is typically performed in equipment known as dryers which can be of the vertical or horizontal type with rotating cylinders. Drying takes place by placing the seeds in contact with a hot flow of gas, generally air, the humidity of which is maintained below the saturation point at the operating temperature. Preferably drying is carried out using dry air at temperatures between 50 and 80° C., preferably 60-70° C.

The seeds undergoing fractionation according to the process according to this invention advantageously have a water content of 4-9% by weight, preferably 4-7%. The said water content is determined using methods of analysis known to those skilled in the art, for example by Karl-Fischer titration or by the method in UNI 22601-1992.

The optional stage of comminution and/or grinding (iv) makes it possible to reduce the volume of the seeds. This stage can be performed by feeding the seeds to equipment capable of reducing the particle size of the seeds, such as for example hammer mills, roller mills, blade mills or slicers, one or several times. The choice of the equipment which has to be used will mainly depend on the dimensions of the seeds and their moisture content.

This optional stage of comminution and/or grinding, together with subsequent mechanical pressing, helps to facilitate extraction stage (b), increasing its efficiency and speed. Performance of at least one mechanical pressing operation on the seeds during stage (a), making it possible to remove significant quantities of oil, in particular makes it possible to minimise solvent use during subsequent extraction stage (b).

The said mechanical pressing operation can advantageously be performed using one or more continuous presses. This operation may take place by feeding the seeds (which may have already been comminuted) at ambient temperature, or, with a view to facilitating oil extraction, preheating the seeds to temperatures generally between 50 and 80° C., preferably 60-70° C., before they enter the press. The increase in pressure generated during pressing generally brings about an increase in internal temperature. Presses may therefore be provided with cooling systems which prevent excessive temperature rise, which could have an adverse effect on the quality of the oil or the solid residue.

Combination of stage (a) and stage (b) in the process according to the invention has the further advantage that it allows pressing to take place under mild conditions (for example limiting pressure and temperature within the press or the number of successive pressing passes), at the same time achieving high extraction yields associated with reduced solvent consumption. This in general gives rise to a high quality extracted oil and solid residue obtained at the end of stage (b).

Various particularly advantageous embodiments will be described below.

According to an advantageous aspect of the invention, a single mechanical pressing operation performed during stage (a) and before extraction stage (b) with a polar organic solvent is sufficient to obtain an effective oil separation, even when operating at ambient temperature. The resulting liquid phase is then subjected to stage (c) to separate the active substances from the residual oil.

According to one particularly preferred embodiment of the process according to the invention, at least two mechanical pressing operations are performed during stage (a) before extraction stage (b) with a polar organic solvent, at least one of which is preferably performed at temperatures between 55 and 75° C. At least one stage of grinding and/or drying the intermediate residue is preferably performed between the at least two aforesaid mechanical pressing operations. One particularly advantageous method of operation for example comprises carrying out the first pressing by feeding the seeds at ambient temperature, drying the first pressing residue at temperatures between 55 and 75° C. and performing a second pressing, feeding the seeds at that temperature.

In the case where the process according to the invention comprises more than one solvent extraction or mechanical pressing operations, it may be advantageous to provide one or more intermediate drying treatments between one operation and another. The purpose of these treatments is to render the extraction operations more efficient.

According to another preferred embodiment, a preliminary grinding treatment is applied to the seeds, followed by a single mechanical pressing operation at temperatures of preferably between 55 and 65° C. (stage a). The residue so obtained subsequently undergoes the stage of extraction with a polar organic solvent (b).

As regards the solvent extraction operations performed in stage (b) of the process and optionally during stage (c), these may be carried out by any technique known to those skilled in the art, for example by immersion, percolation or using a counter-current extraction system. The first residue obtained from stage (a) is placed in contact with a polar organic solvent during stage (b) which extracts the oil and active substances from it.

The process of the invention is preferably performed without having recourse to any washing or extraction of the first residue of step (a) with water, in order not to extract the water-soluble proteins and to maintain a high protein content in the solid residue of step (b). The polar organic solvents generally used to perform the extraction in stage (b) are selected from methanol, ethanol, propanol, isopropanol, 1-butanol, 2-butanol, isobutanol and higher alcohols their esters with acetic acid or propionic acid (for example methyl acetate, ethyl acetate, propyl acetate, isopropyl acetate, butyl acetate, isobutyl acetate, tert-butyl acetate, pentyl acetate, hexyl acetate, methyl propionate, ethyl propionate, propyl propionate, isopropyl propionate, butyl propionate, pentyl propionate etc.), acetonitrile, acetone, methyl ethyl ketone, diethyl ketone, ethyl propyl ketone, THF or 2-methoxyethanol (methylcellosolve). Extraction with polar organic solvents is typically performed at temperatures above ambient temperature and below or equal to the boiling point of the solvent. The weight ratio between the polar organic solvent and the first residue obtained from stage (a) is advantageously of between 1:1 and 4:1, preferably of between 1:1 and 3:1 and more preferably of 1:1 and 2:1.

Among polar organic solvents, those which do not form azeotropes or which require small amounts of water for the formation of an azeotrope are preferred.

Traces of water can be present during the extraction operations of step (b), in amounts depending on the solvent used and preferably not higher than those required for the azeotrope formation.

The extraction of step (b) is preferably performed using ethanol or higher alcohols as solvent. Even more preferably this is performed using ethanol or isopropanol, which have the particular advantage of maintaining a high protein content in the solid residue by extracting the residual oil and not extracting the water-soluble proteins. In the case of the extraction with ethanol, it is typically performed at temperatures of around 60-80° C., with the ratio between ethanol and the crushed seeds (originating from stage (a) after mechanical pressing) of advantageously between 1-4:1, preferably between 1.5-2.5:1 by weight.

According to a preferred embodiment of the process, extraction stage (b) is carried out by immersion in ethanol (or isopropanol) and reflux heating for a time of between 30 minutes and 2 hours, then separating off the ethanol (or isopropanol) extract for example by filtration. Before undergoing the separation stage (c) the liquid phase resulting from stage (b), comprising oil and active substances extracted from the residue from stage (a), is preferably concentrated using known techniques, for example by distillation and/or evaporation, typically under vacuum. This makes it possible to recover the solvent, which can thus be reused several times for subsequent extraction operations.

According to a particularly preferred embodiment stage (c) comprises extraction with an apolar solvent performed on the liquid phase obtained from stage (b), suitably concentrated, with subsequent separation of the apolar fraction comprising oil from the polar fraction containing active substances. The said extraction with apolar solvent is typically performed at temperatures of between ambient temperature and 80° C., even more preferably at ambient temperature, possibly making use of suitable agitation systems or other systems suitable for breaking up clumps of product and obtaining suitable mixing with the solvent. Examples of apolar solvents which are suitable for performing this extraction are hydrocarbons such as hexane and petroleum ether. Preferably extraction with apolar solvent is performed using petroleum ether.

Before undergoing an extraction with apolar solvent during stage (c) the liquid phase resulting from stage (b), comprising oil and active substances, is advantageously concentrated, removing the polar organic solvent. In this way, when the apolar solvent is added the polar fraction comprising active substances, the latter are solid and are advantageously separated from the liquid apolar fraction comprising oil, for example by filtration.

According to another preferred embodiment of the process according to this invention stage (c) comprises crystallisation of the active substances, which may be performed from the liquid phase obtained in stage (b) as such or after partial concentration of the polar organic solvent, which is preferably selected from acetone and isopropanol. After crystallisation the active substances are advantageously separated by filtration and the extract may undergo further treatments for recovery of the oil present therein.

According to another preferred embodiment the liquid phase from stage (b) is partly concentrated and then the active substances present in it undergo hydrolysis, for example by the addition of an aqueous solution of an inorganic acid (e.g. $H_2SO_4$) or by means of resins, in order to remove the carbohydrate component. The active substances may then be separated out as aglycones (e.g. Arctigenin, Trachelogenin) during stage (c) of the process. The active substances so obtained can be separated out and purified by means of known techniques, for example by chromatographic separation and/or filtration on silica.

The oil obtained from the process according to the invention may possibly be treated and purified, typically by means of settling, filtration or centrifuging. Typically the oil obtained by solvent extraction during stage (c) undergoes distillation in order to recover the solvent, which can thus be used several times for successive extraction operations. The purified oil obtained may therefore be possibly pooled with that originating from stage (a) and used (directly or after selective hydrogenation treatment in order to maximise the monounsaturated fatty acids content) in order to produce biofuels and for the production of chemical intermediates such as carboxylic acids and their derivatives.

As far as the solid residue obtained at the end of stage (b) is concerned, this is typically separated from the extract by filtration or centrifuging or by means of other techniques known to those skilled in the art. The process may provide for one or more washes of the solid residue. The solvent is then removed by suitable recovery treatments carried out in equipment such as for example evaporators or solvent extractors.

Typically this recovery stage is performed by making use of the volatility of the solvent and therefore by applying heat, by reducing pressure or a combination of the two. The solid residue obtained in stage (b) of the process according to this invention has a protein content higher than 20% by weight, preferably of between 20 and 40% by weight and more preferably between 20 and 35% by weight, and an oil content advantageously of less than 10%, preferably less than 5%, more preferably less than 2%, even more preferably less than 0.5%, as determined after acid hydrolysis according to method UNI 22605-1992.

The protein content of the solid residue can be further increased by subjecting it to one or more optional mechanical or electrochemical separation operations, in order to separate a fraction richer in proteins from a fraction richer in cellulose, hemicellulose and lignin. For example the solid residue is screened by passing it through vibrating screens or sieves, aspiration systems or electromagnetic systems. A specific example of the said optional operation is the electrostatic separation treatment preceded by ultrafine milling described in Chem Sus Chem 2015, 8, 1161-1166.

The proteins present in the said solid residue also have high nutritional value. An analysis of protein content using the CNCPS (Cornell Net Carbohydrates and Protein System) system has in fact demonstrated that these proteins are principally of the B2 and B3 types, that is proteins which are insoluble (B2) or can potentially be degraded associated with neutral detergent fibre (B3).

In particular when seeds of *Cynara cardunculus* undergo the process according to the invention it has also surprisingly been found that the B2 and B3 protein content of the said residue is decisively greater than in both the seed and in the first residue from mechanical pressing, together with an appreciable reduction in the content of type B1 protein (immediately degradable cytoplasmic soluble protein) without at the same time giving rise to an increase in the content of type C proteins, which are indigestible. This reduced concentration of B1 proteins thus helps to reduce the rate at which the protein component is degraded without prejudicing its digestibility.

A further advantageous feature of the solid residue obtained in stage (b) from *Cynara cardunculus* is represented by its marked antioxidant activity, which is related to the phenolic compounds content and particularly to the polyphenols content. For example a proper polyphenol intake by animals such as ruminants has a known positive effect on their health and their production performance, as well as on the oxidative stability of the products derived therefrom.

Thanks to the high balanced protein content and the reduced risk of it turning rancid because of the low oil content the said solid residue is particularly suitable for use as a component of feedstuffs for livestock, for example for aquaculture.

Besides the high nutritional value, the solid residue has surprisingly shown a high palatability by livestock, probably due to its significantly low oil and/or lipophilic flavours content. Depending upon the type of animals for which the said feeds are intended, the solid residue according to this invention may advantageously be mixed with other nutritional components such as for example fibres, fats, mineral salts, carbohydrates and vitamins.

Thanks to the high organic nitrogen content the solid residue obtained in stage (b) may also advantageously be reused in agriculture, for example for the preparation of fertilisers.

The active substances extracted from seeds according to the invention in polar organic solvent and subsequently separated from the extracted liquid phase are typically in form of a mixture rich in polyphenols such as lignans and flavonolignans. Preferably the said active substances comprise lignans belonging to the group comprising Arctiin, Tracheloside and corresponding aglycones.

According to a preferred aspect the extracted active substances comprise both Arctiin and Tracheloside. For example when seeds from *Cynara cardunculus* are fractionated according to the process of the present invention, the said active substances advantageously comprise Arctiin and Tracheloside in similar weight ratios.

According to another aspect, the active substances advantageously comprise one or more substances selected from Arctiin, Arctigenin, Tracheloside, Trachelogenin, Cynarine, Cynarinine, Chlorogenic acid, Nortrachelogenin guaiayacylglyceryl ether, Silibinin, Isosilibinin, Silicristin, Silidianin, N-(p-coumaroyl)serotonin glucoside, N-feruloylserotonin glucoside, and their isomers.

The present invention therefore refers also to a mixture of active substances comprising Arctiin and Tracheloside. The Tracheloside/Arctiin weight ratio is preferably between 50/1 and 1/50. The said weight ratio can be calculated for example after quantification of Arctiin and Tracheloside by HPLC analysis.

Advantageously the Tracheloside/Arctiin weight ratio within the active substances of the invention is preferably of from 0.6 to 1.5, more preferably from 0.7 to 1.3, even more preferably from 0.8 to 1.2. Preferably the said mixture additionally comprise one or more substances selected from Arctigenin, Trachelogenin, Cynarine, Cynarinine, Chlorogenic acid, Nortrachelogenin guaiayacylglyceryl ether, Silibinin, Isosilibinin, Silicristin, Silidianin, N-(p-coumaroyl)serotonin glucoside, N-feruloylserotonin glucoside, and their isomers.

The said active substances separated out during stage (c) of the process may advantageously be used, as such or after suitable treatments to isolate the molecules of interest, as cosmetic, dermatologic, nutraceutical and/or pharmaceutical ingredients, or as biostimulants.

The lignans in glucoside form in particular, such as for example Arctiin and Tracheloside, may undergo hydrolysis and possible purification operations to isolate the corresponding aglycones from the carbohydrate components.

The said hydrolysis may for example be performed by means of enzymes or in an acid environment through the addition of inorganic acids (e.g. $H_2SO_4$) or using resins. The hydrolysed active substances may for example be purified by chromatography, by filtration on silica or by vacuum chromatography.

The process according to the invention will now be described on the basis of a non-limiting examples.

EXAMPLES

Example 1

(Stage a)

200 kg of seeds of *Cynara cardunculus* were cleaned, screened and subsequently dried to a water content of 6.6% by weight.

The said seeds were fed to a single screw press (Mod. MIG PC25S screw diameter=110 mm; L/D=4.4) operating at 20 rpm at ambient temperature with a throughput of 75.8 kg/h yielding 38.8 kg of oil and approximately 158 kg of a first intermediate residue (containing the approximately 7.5% by weight of water). The said residue was dried in a 3 tray dryer (diathermic oil T=170° C.; residence time=55 minutes) at approximately 60° C. until the water content was 2.4%. The intermediate residue dried in this way was again fed to the same previously used single screw press operating at 10 rpm at a temperature of 60° C. with a throughput of 45 kg/h, yielding 5.35 kg of oil and 145.8 kg of a second residue comprising de-oiled seeds having an oil content of approximately 4% by weight.

(Stage b)

1 kg of the de-oiled residue so obtained was then extracted with ethanol (residue/ethanol ratio=1/2 by weight) under reflux for one hour in a reactor provided with a mechanical stirrer. The suspension obtained was filtered and washed with ethanol (200-300 ml). The solid phase was dried overnight in a stove at a temperature of 80° C.

A solid residue weighing 835 g having the following composition was obtained:
oil: 0.3% by weight;
protein content: 27% by weight.

(Stage c)

The ethanol extract (liquid phase) obtained from stage (b) was dried in a rotary evaporator yielding an orange-coloured pasty solid which was then extracted with petroleum ether (300-400 ml) at ambient temperature in a reactor fitted with a mechanical stirrer so as to obtain a homogeneous dispersion which was then filtered.

The apolar fraction separated out in this way was then dried, yielding 42 g of oil.

The polar fraction was twice washed with petroleum ether (200 ml) and dried to constant weight with air, yielding 112 g of an orange-coloured solid.

A 200 ppm (w/vol) solution of the said solid in acetonitrile was analysed by HPLC-MS, performed using a liquid chromatograph fitted with a Kinetex 1.7μ XB-C18 100 Å 100× 2.10 mm Phenomenex column, with a UV-PDA recorder interfaced with an ion trap spectrometer (LCQ Fleet Thermo Scientific; ESI ionisation method, positive/negative ions), with the following instrument conditions:

Eluents: (A) 1% aqueous solution of HCOOH; (B) acetonitrile
Gradient: 0 min (A/B=95/5), 5 min (A/B=90/10), 20 min (A/B=60/40), 30 min (A/B=10/90), 40 min (A/B=10/90), 45 min (A/B=95/5);
Flow rate 0.4 ml/min;
Detector: UV-PDA 280 nm.

HPLC/UV analysis of the said solid revealed the presence of Arctiin (30% by weight with respect to the solid), the identity of which was confirmed from the mass spectrum (m/z 535 [M+H]$^+$). The total content of glucosides, all quantified as Arctiin, on the other hand corresponded to approximately 60% by weight with respect to the weight of the solid.

Example 2

(Stage a)

200 kg of seeds of *Cynara cardunculus* were cleaned and screened.

The said seeds with a water content of 7.5% by weight were fed to a single screw press (Mod. MIG PC25S screw diameter=110 mm; L/D=4.4) operating at 20 rpm at ambient temperature with a throughput of 60.9 kg/h, yielding 32.7 kg of oil and approximately 167 kg of a residue (containing the approximately 9% by weight of water). The said residue comprising de-oiled seeds had an oil content of approximately 10% by anhydrous weight.

(Stage b)

1 kg of the obtained residue was then extracted with 1.6 kg of anhydrous ethanol under reflux for one hour in a reactor provided with a mechanical stirrer. The suspension obtained was filtered and washed with ethanol (200-300 ml). The solid phase was dried overnight in a stove at a temperature of 80° C.

A solid residue weighing 790 g was obtained.

(Stage c)

The ethanol extract (liquid phase) obtained from stage (b) was dried in a rotary evaporator yielding 240 g of an orange-coloured pasty solid which was then extracted with hexane (300-400 ml) at ambient temperature in a reactor fitted with a mechanical stirrer so as to obtain a homogeneous dispersion which was then filtered.

The polar solid fraction was twice washed with hexane (200 ml) and dried to constant weight with air, yielding 106 g of an orange-coloured solid.

The hexane liquid fractions were then collected and dried, yielding 98 g of oil.

Examples 3-6

(Stage a)

200 kg of seeds of *Cynara cardunculus* were cleaned and screened.

The said seeds with a water content of 7.5% by weight were fed to a single screw press (Mod. MIG PC25S screw diameter=110 mm; L/D=4.4) operating at 34 rpm at ambient temperature with a throughput of 58.5 kg/h, yielding 41.3 kg of oil and approximately 157 kg of a residue (containing the approximately 8.5% by weight of water). The said residue comprising de-oiled seeds had an oil content of approximately 6% by anhydrous weight.

(Stage b)

Four polar organic solvents (anhydrous ethanol, hydrous ethanol (i.e. 95% ethanol and 5% water), isopropanol, acetone) were each tested for the extraction of 1 kg of the de-oiled residue obtained in stage a) as describe above.

Each extraction was performed under reflux for one hour in a reactor provided with a mechanical stirrer; the residue/solvent ratio was 1/2 by volume.

The suspensions obtained were filtered and washed with the same solvent used for the extraction.

The solid phases were then dried overnight as in Examples 1-2; the weights of the obtained solid residues are reported in Table 1.

(Stage c)

The liquid phase of Examples 3-6 were dried in a rotary evaporator; the pasty solid was then washed three times with hexane and subsequently dried. The total weight of solid active substances and of the oil recovered after evaporation of the hexane fractions are reported in Table 1.

The active substances obtained in Examples 3-6 were analysed by HPLC-UV as described in Example 1. The analysis of the samples revealed the presence of Arctiin and Tracheloside; the identity of the latter was confirmed from the mass spectrum (m/z 551 [M+H]$^+$). The amounts of Arctiin and Tracheloside (both quantified as Arctiin) within the extracted active substances are reported in Table 1: the Tracheloside/Arctiin weight ratio is of approximately of 1:1 (about 0.9) in all Examples 3-6.

The protein content of the extracted active substances was calculated by determining the nitrogen content (by means of Kjeldhal method) and multiplying the obtained value by the coefficient 6.25.

| Ex-ample | Solvent | Solid residue (g) | Oil (g) | Tot. (g) | Pro-tein (g) | Arctiin (g) | Tracheloside (g) |
|---|---|---|---|---|---|---|---|
| 3 | anhydrous ethanol | 837 | 56 | 107 | 2.2 | 29.5 | 28.7 |
| 4 | ethanol 95%* | 812 | 47 | 140 | 2.5 | 32.4 | 31.6 |
| 5 | iso-propanol | 849 | 61 | 77 | 1.1 | 32.1 | 30.3 |
| 6 | acetone | 871 | 56 | 58 | 1.1 | 22.5 | 20.7 |

*water content of 5% by weight relative to the total weight of solvent.

As can be seen from Table 1, isopropanol allowed to extract Arctiin with a purity of about 42% by weight (32.1 g over 77 g tot. active substances), i.e. a purity higher than that attained with other solvents.

Example 7

(Stage a)
200 kg of seeds of *Carthamus tinctorius* were cleaned and screened.

The said seeds having a water content of 7% by weight were fed to the same screw press of Examples 1-6, operating at 20 rpm at ambient temperature with a throughput of 49.7 kg/h, yielding 64.1 kg of oil and approximately 135.2 kg of a residue (containing the approximately 9.7% by weight of water). The said residue comprising de-oiled seeds had an oil content of approximately 11.5% by anhydrous weight.

(Stage b)
1 kg of the de-oiled residue so obtained was then extracted with anhydrous ethanol (residue/ethanol ratio=1/1.6 by weight) under reflux for one hour in a reactor provided with a mechanical stirrer. The suspension obtained was filtered and washed with ethanol (200-300 ml). The solid phase was dried overnight in a stove at a temperature of 100° C.

A solid residue weighing 864 g having a protein content of 21.5% by weight was obtained.

(Stage c)
The ethanol extract (liquid phase) obtained from stage (b) was dried in a rotary evaporator yielding a pasty solid which was then extracted with hexane at ambient temperature in a reactor fitted with a mechanical stirrer. The obtained emulsion was centrifuged at 3000 rpm for 10 minutes.

The apolar fraction separated out in this way was then dried, while the polar solid fraction was washed with hexane and dried to constant weight with air, yielding 24.9 g of a yellow solid. The hexane fraction was also dried in the same manner, yielding 101 g of oil.

The HPLC-MS analysis of the solid revealed the presence of Arctiin, Tracheloside and of the serotonin derivatives N-(p-coumaroyl)serotonin glucoside (m/z 485 [M+H]$^+$) and N-feruloylserotonin glucoside (m/z 515 [M+H]$^+$). According to the HPLC-UV analysis, the solid contained about 0.75% by weight of Arctiin and 16% by weight of Tracheloside with respect to the weight of the solid.

The invention claimed is:

1. A process for the fractionation of seeds of an oleaginous plant of the Asteraceae family into oil, solid residue and active substances comprising the steps of:
    (a) subjecting said seeds to at least one mechanical pressing operation, removing at least a portion of the oil and obtaining a first residue;
    (b) subjecting said first residue to extraction with a polar organic solvent and separating the remaining solid residue from the resulting liquid phase comprising oil and extracted active substances;
    (c) separating the active substances and oil from said liquid phase of step b),
wherein the extraction of step b) is performed at temperatures above ambient temperature and below or equal to the boiling point of the solvent and wherein the weight ratio between the polar organic solvent and the first residue is from 1:1 to 4:1.

2. The process according to claim 1 wherein the step (c) comprises the addition of an apolar solvent and subsequent separation of an apolar fraction comprising oil from a polar fraction comprising the active substances.

3. The process according to claim 1 comprising, prior to step (a) at least a preliminary stage of treatment of the seeds selected from:
    (i) cleaning and sieving;
    (ii) decortication;
    (iii) drying;
    (iv) comminuting and/or grinding.

4. The process according to claim 1, comprising a single mechanical pressing operation before the step (b).

5. The process according to claim 1, comprising at least two operations of mechanical pressing before the step (b), at least one of which conducted at temperatures from 55-75° C.

6. The process according to claim 5 comprising at least a step of grinding and/or drying of the intermediate solid residue between the at least two operations of mechanical pressing.

7. The process according to claim 1, wherein said oleaginous plant of the Asteraceae family belongs to the Cardueae tribe.

8. The process according to claim 1, wherein said polar organic solvent is selected from, methanol, ethanol, isopropanol, isobutanol and higher alcohols, their esters with acetic and propionic acids, acetonitrile, acetone, methyl ethyl ketone, diethyl ketone, ethyl propyl ketone, THF, 2-methoxyethanol.

9. The process according to claim 8, wherein said polar organic solvent is ethanol or isopropanol.

10. The process according to claim 2, wherein said apolar solvent is selected from petroleum ether and/or hexane.

11. A solid residue resulting from the seeds of an oleaginous plant of the Asteraceae family and obtainable from step b) of the process according to claim 1, having a protein content higher than 20% by weight and an oil content of less than 10%,
wherein said oleaginous plant is *Cynara cardunculus*.

12. A method for producing animal feed which comprises adding the solid residue according to claim 11 to the animal feed.

13. An animal feed comprising the solid residue according to claim 11, fiber, fat, minerals, carbohydrates, vitamins.

14. An active substance obtained from step c) of the process according to claim 1 in a form of a mixture rich in polyphenols characterized by the presence of Arctiin and Tracheloside in a weight ratio of 0.6 to 1.5, wherein said oleaginous plant is *Cynara cardunculus*.

15. The active substance according to claim 14 further comprising one or more substances selected from Arctigenin, Trachelogenin, Cynarine, Cynarinine, Chlorogenic acid, Nortrachelogenin guaiayacylglyceryl ether, Silibinin, Isosilibinin, Silicristin, Silidianin, N-(p-coumaroyl)serotonin glucoside, N-feruloylserotonin glucoside, and their isomers.

16. A composition comprising the active substance according to claim 14 as a cosmetic ingredient, or as biostimulant.

17. The process according to claim 2 comprising, prior to step (a) at least a preliminary stage of treatment of the seeds selected from:
   (v) cleaning and sieving;
   (vi) decortication;
   (vii) drying;
   (viii) comminuting and/or grinding.

18. The process according to claim 2, comprising a single mechanical pressing operation before the step (b).

19. The process according to claim 3, comprising a single mechanical pressing operation before the step (b).

20. The process according to claim 2, comprising at least two operations of mechanical pressing before the step (b), at least one of which conducted at temperatures from 55-75° C.

21. The active substance according to claim 14, wherein the weight ratio of Arctiin to Tracheloside is 0.7 to 1.3.

22. The active substance according to claim 14, wherein the weight ratio of Arctiin to Tracheloside is 0.8 to 1.2.

* * * * *